United States Patent [19]

Kvita

[11] Patent Number: 5,004,814
[45] Date of Patent: Apr. 2, 1991

[54] SUBSTITUTED α-PYRONES AND PROCESS FOR THEIR PREPARATION

[75] Inventor: Vratislav Kvita, Reinach, Switzerland

[73] Assignee: Ciba-Geigy Corporation, Ardsley, N.Y.

[21] Appl. No.: 421,573

[22] Filed: Oct. 16, 1989

[30] Foreign Application Priority Data

Nov. 15, 1988 [CH] Switzerland .................... 4224/88

[51] Int. Cl.$^5$ .................................... C07D 309/38
[52] U.S. Cl. .................................................. 549/294
[58] Field of Search ......................................... 549/294

[56] References Cited

PUBLICATIONS

*Registry Hanbook* No. 41819-58-3 (1973).
Ingold et al., J. Chem. Soc. 121, 1638–48 (1922).
W. A. Boulanger et al., J. Med. Chem. vol. 29 pp. 1159–1163 (1986).
A Roedig et al., Liebigs Ann. Chem. vol. 636 pp. 1–18 (1961).

*Primary Examiner*—Frederick E. Waddell
*Attorney, Agent, or Firm*—Michael W. Glynn; Stephen V. O'Brien; Edward McC. Roberts

[57] ABSTRACT

The invention relates to α-pyrones of formula I

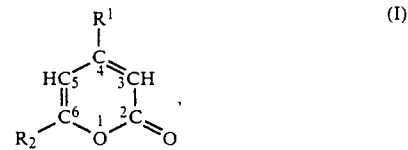

wherein $R^1$ is chloro or bromo and $R^2$ is hydrogen, chloro or bromo. The halogen in 4-position can be replaced, for example, by alkoxy, alkylthio or secondary amino. The α-pyrones are suitable diene components for Diels-Alder reactions.

3 Claims, No Drawings

SUBSTITUTED α-PYRONES AND PROCESS FOR THEIR PREPARATION

The present invention relates to 4- or 4,6-chlorinated or brominated α-pyrones and to a process for the preparation of 4-chloro- or 4-bromo-α-pyrones.

In J. Med. Chem., 29, 1159–1163 (1986), W. A. Boulanger et al. describe the preparation of 4-phenyl-6-chloro-α-pyrone and the reduction thereof with zinc and glacial acetic acid to give 4-phenyl-α-pyrone. In Liebigs Ann. Chem., Vol. 636, 1–18 (1961), A. Roedig et al. mention that, in perchloro-α-pyrone, the mobile chlorine atoms in 4- and 6-position can be readily removed by reduction with zinc and acetic acid.

In contradistinction thereto, it has now been found that the reduction of α-pyrones which are substituted in 4- and 6-position by chloro and/or bromo gives 4-chloro- and 4-bromo-α-pyrone, respectively, in good yield and high selectivity.

In one of its aspects, the present invention relates to α-pyrones of formula I

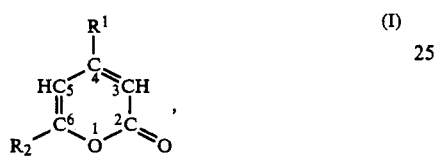

wherein $R^1$ is chloro or bromo and $R^2$ is hydrogen, chloro or bromo.

$R^1$ is preferably chloro and $R^2$ is preferably hydrogen or chloro. Particularly preferred compounds are 4-chloro-α-pyrone and 4,6-dichloro-α-pyrone.

In another of its aspects, the invention relates to a process for the preparation of α-pyrones of formula Ia

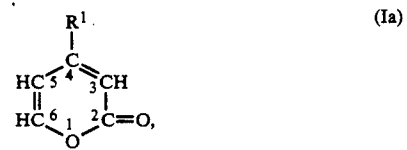

wherein $R^1$ is chloro or bromo, which process comprises reducing an α-pyrone of formula Ib

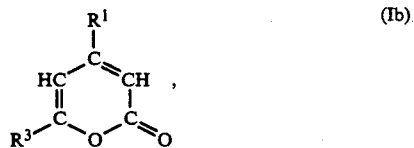

wherein $R^1$ is chloro or bromo and $R^3$ is chloro or bromo, with hydrogen.

The reduction is known per se and is described, for example, in J. Med. Chem., 29, 1159–1163 (1986). For the reduction it is preferred to use nascent hydrogen, which is produced in a manner known per se by treating a metal with an acid, for example with Zn/HCl, and preferably with Zn/acetic acid. It is preferred to use an excess of acetic acid, which then simultaneously acts as solvent.

It is, however, also possible to use inert solvents, for example aprotic and, in some cases, polar solvents. Examples of such solvents are hydrocarbons (petroleum ether, pentane, hexane, cyclohexane, methyl cyclohexane), and ethers (diethyl ether, dibutyl ether, dioxane, tetrahydrofuran, ethylene glycol dimethyl ether).

The reaction temperature may be in the range from 20° to 100° C. The process can be carried out by dissolving the 4,6-dihalogenated α-pyrone in an acid and with or without an inert solvent, and adding the metal in portions or in one portion. After the exothermic reaction has subsided, the reaction can be brought to completion by stirring for several hours. The metal is conveniently added in equivalent amounts.

To isolate the desired product, an excess of the acid employed can first be removed by distillation or vacuum distillation, together with a solvent. If a solvent is concurrently used, the reaction mixture or the distillation residue taken up in a solvent can be neutralised direct, for example by addition of $KHCO_3$. Isolation and purification can be effected by conventional methods, for example by distillation, recrystallisation or by chromatographic methods.

The compounds of formula Ib can be obtained in a manner known per se by cyclising glutaconic acids of formula II

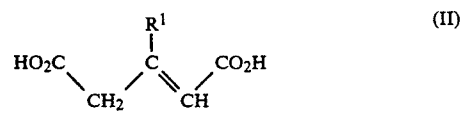

with, for example, acetyl chloride, thionyl chloride, $PCl_3$, $PCl_5$ or $PBr_3$.

The preparation is described in J. Med. Chem., 29, 1159–1163 (1986). The preparation of the glutaconic acids of formula II is described, for example, in J. Chem. Soc., 121, 1638 1648 (1922).

Surprisingly, in the compounds of formula Ia the chlorine or bromine atom can be substituted with nucleophilic compounds, in which substitution only negligible attack occurs at the nucleophilic CH group in 6-position. Examples of suitable nucleophilic compounds are secondary amines, aliphatic and aromatic alcohols or mercaptans or alkali metal salts thereof, as well as alkali metal sulfinates. Examples of suitable alkali metals are Li, Na and K.

The compounds of formula Ia and their derivatives which carry nucleophilic substituents are useful diene components for Diels-Alder reactions. The reaction with 1,4-anthraquinones leads to 2-substituted naphthacene-5,12-diones, among which in particular the naphthacene-5,12-diones substituted with a mercaptan are excellent photoinitiators or photosensitisers for ethylenically unsaturated photopolymerisable or photodimerisable compounds.

The invention is illustrated by the following Examples.

(A) PREPARATORY EXAMPLES

Example 1: 4,6-Dichloro-2-oxo-2H-pyran (4,6-dichloro-α-pyrone)

114.93 g (0.699 mol) of 3-glutaconic acid are added to 291.15 g (1.398 mol) of ice-cooled $PCl_5$. A vigorous reaction ensues, with strong evolution of HCl gas, and a red solution forms. The reaction mixture is stirred for 15 minutes at 100° C. and the resultant $POCl_3$ is removed by distillation in a water jet vacuum at 40° C. The residue is taken up in 2000 ml of $CH_2Cl_2$ and, after extraction with water, the aqueous extract is filtered through Hyflo. The organic solution is stirred in aqueous NaHCO$_3$ solution, while ensuring that the pH does not exceed 7-7.5. The organic phase is dried over Na$_2$SO$_4$, concentrated at 45° C. in a water jet vacuum, and the residue is distilled at a bath temperature of 80°-100° C./0.05 mbar in a U-flask. Yield: 27.6 g (71.9%); melting point: 43°-45° C.

Example 2: 4-Chloro-2-oxo-2H-pyran (4-chloro-α-pyrone)

To a solution of 49.5 g (0.3 mol) of 4,6-dichloro-2-oxo-2H-pyrane in 150 ml of acetic acid are added 21.6 g (0.3 mol) of Zn in one portion. After the ensuing exothermic reaction has subsided, the reaction mixture is stirred for 2 hours. The acetic acid is removed by distillation at 50° C. in a water jet vacuum, and the residue is taken up in 300 ml of CH$_2$Cl$_2$. After addition of 100 ml of water, KHCO$_3$ is added in portions, with efficient stirring, until the pH is 7. The organic phase is separated, and the aqueous solution is extracted with 2×100 ml of CH$_2$Cl$_2$. The combined organic phases are dried over Na$_2$SO$_4$ and concentrated. The distillation residue is filtered with suction and the crystalline residue is washed with ether. The mother liquors are chromatographed over silica gel (eluant: CH$_2$Cl$_2$). Total yield: 12.43 g (31.7% of theory). Melting point: 56°-58° C.

(B) USE EXAMPLE

(a) 4-Benzylthio-2-oxo-2H-pyran (4-benzylthio-α-pyrone)

To a solution of 0.433 g (0.0033 mol) of 4-chloro-2-oxo-2H-pyran and 0.41 g (0.0033 mol) of benzyl mercaptan in 2 ml of dimethyl formamide is added 0.228 g (0.00165 mol) of K$_2$CO$_3$. The reaction mixture is stirred for 1 hour and then the same amount of K$_2$CO$_3$ is once more added. The reaction mixture is then stirred overnight at 25° C., diluted with 30 ml of CH$_2$C$_2$, and extracted with 5×50 ml of a saturated aqueous solution of NaCl. The organic phase is dried over Na$_2$SO$_4$ and concentrated in a water jet vacuum. The distillation residue is chromatographed over silica gel. Yield: 0.36 g (50%). Melting point: 105°-106° C.

(b) 2-Benzylthionaphthacene-5,12-dione

A mixture of 0.27 g (0.0012 mol) of 4-benzylthio-2-oxo-2H-pyrane, 0.25 g (0.0012 mol) of 1,4-anthraquinone and 0.10 g (0.0012 mol) of MnO$_2$ in 5 ml of dichlorobenzene is heated for 24 hours under reflux (180° C.), then cooled and chromatographed over silica gel. Using cyclohexane as eluant, dichlorbenzene is first extracted, then the crude product is chromatographed with CH$_2$Cl$_2$. The pre-purified product is chromatographed once more, using CH$_2$Cl$_2$ as eluant, and the solvent is removed by evaporation. Yield: 0.09 g (20%). Melting point: 200°-203° C.

(c) Photocuring of an Acrylate Mixture for the Production of a Relief Image

A photocurable composition is prepared by mixing the following components:

|  | Solids content |
|---|---|
| 150.30 g of Scripset 540$^{(1)}$ (30% solution in acetone) | 45.1 g |
| 48.30 g of trimethylolpropane triacrylate | 48.3 g |
| 6.60 g of polyethylene glycol diacrylate | 6.6 g |
| 0.08 g of crystal violet |  |
| 205.28 g | 100.0 g |

$^{(1)}$polystyrene maleic acid half-ester copolymer (Monsanto)

Portions of this composition are mixed with 0.2% (based on the composition) of 2-benzylthionaphthacene-5,12-dione. All operations are carried out under red or yellow light.

The samples are applied with a helical doctor of 150 μm to a 200 μm aluminium sheet (10×15 cm). The solvent is removed by heating for 15 minutes to 60° C. in a drying oven, to give a dry layer thickness of 35 μm. A 76 μm polyester sheet is laid on the layer and then a standardised test negative with 21 steps of different optical density (Stouffer wedge) is placed on the polyester sheet. Over this negative is then placed a second polyester sheet, and the laminate so obtained is affixed by vacuum to a metal plate. The sample is then exposed with a 5 Kw metal halide lamp (MO 23 type) at a distance of 30 cm. Exposure is made in a first test run for 20 seconds and in a second test run for 40 seconds. After exposure, the sheets and the mask are removed and the exposed layer is developed for 2 minutes in an ultrasonics bath with developer A, and then dried at 60° C. for 15 minutes in a drying oven. The sensitivity of the initiator system is characterised by indicating the last wedge step which has been reproduced tack-free. The higher the number of steps, the more sensitive the system. An increase of two steps means that the curing rate has been approximately doubled. The number reproduced steps is 1 after exposure for 20 s and 4 after exposure for 40 s. (Developer A contains 15 g of sodium metasilicate.9H$_2$O, 0.16 g of KOH, 3 g of polyethylene glycol 6000, 0.5 g of livulinic acid and 1000 g of deionised water).

What is claimed is:

1. An α-pyrone of formula I

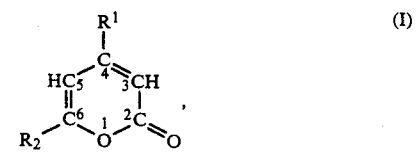

wherein R$^1$ is chloro or bromo and R$^2$ is hydrogen, chloro or bromo.

2. An α-pyrone of formula I according to claim 1, which is 4-chloro-α-pyrone.

3. An α-pyrone of formula I according to claim 1, which is 4,6-dichloro-α-pyrone.

* * * * *